United States Patent [19]
Brinon

[11] Patent Number: 5,380,306
[45] Date of Patent: Jan. 10, 1995

[54] UNITARY COMPOSITE CONNECTOR FOR A LIQUID CIRCUIT, IN PARTICULAR FOR MEDICAL APPLICATIONS

[75] Inventor: Thierry Brinon, Ecouen, France

[73] Assignee: Vygon, Ecouen, France

[21] Appl. No.: 980,547

[22] Filed: Nov. 23, 1992

[30] Foreign Application Priority Data

Nov. 25, 1991 [FR] France ................... 91 14492

[51] Int. Cl.⁶ .................................. A61M 5/00
[52] U.S. Cl. ...................... 604/244; 604/905; 128/764
[58] Field of Search ............... 604/905, 244, 245, 283, 604/256, 411, 414, 82, 83, 86–88, 200; 137/68.1; 251/199.6; 128/764, 766, 770

[56] References Cited

U.S. PATENT DOCUMENTS

| | | | |
|---|---|---|---|
| 3,352,531 | 11/1967 | Kilmarx | 604/99 X |
| 3,399,677 | 9/1968 | Gould et al. | 604/99 |
| 4,781,702 | 11/1988 | Herrli | 604/244 |
| 4,893,636 | 1/1990 | Cook et al. | 128/764 |
| 4,920,976 | 5/1990 | Calzi et al. | 128/764 |
| 4,998,927 | 3/1991 | Vaillancourt | 604/283 |
| 5,065,783 | 11/1991 | Ogle | 137/68.1 |
| 5,092,840 | 3/1992 | Healy | 604/83 |
| 5,122,123 | 6/1992 | Vaillancourt | 604/192 |
| 5,127,904 | 7/1992 | Loo et al. | 604/83 |
| 5,154,703 | 10/1992 | Bonaldo | 604/244 |

FOREIGN PATENT DOCUMENTS

3809127  4/1989  Germany ................... 604/283

Primary Examiner—C. Fred Rosenbaum
Assistant Examiner—V. Alexander
Attorney, Agent, or Firm—Mason, Kolehmainen, Rathburn & Wyss

[57] ABSTRACT

A hollow needle fixed in a chamber establishes a connection between an upstream coupling and a downstream coupling when it passes through a plug. The plug is made of a material such that it regains its closure properties when the needle is no longer passing through it, and it is pushed away from the needle by a spring to a closure position in which it fills the outlet opening of the downstream coupling. The connector is particularly suitable for use in medical applications.

21 Claims, 10 Drawing Sheets

FIG_1

FIG_2

FIG_3

FIG_7

FIG_8

FIG_9

FIG_10

FIG_11

FIG_12

FIG_13

FIG_16B

FIG_16A

FIG_17

FIG_18

FIG_19

UNITARY COMPOSITE CONNECTOR FOR A LIQUID CIRCUIT, IN PARTICULAR FOR MEDICAL APPLICATIONS

The invention relates to a unitary composite connector for a liquid circuit, in particular for medical applications.

The term "unitary" means that the connector is constituted by a permanent assembly, unlike certain prior art connectors which are constituted by at least two separate subassemblies that are assembled together when the connection is established.

BACKGROUND OF THE INVENTION

More particularly, the invention relates to a connector of the type that comprises a unitary composite connector for a liquid circuit, in particular for medical applications, the connector comprising: means constituting a tubular chamber between an upstream coupling and a downstream coupling situated at opposite ends of the chamber and fixed relative to each other, said upstream coupling constituting a passage; a hollow needle which is fixed in the chamber and which is suitable for causing the upstream coupling to communicate with the downstream coupling; and a plug suitable for being passed through by the needle, the plug being mounted in the passage of the downstream coupling so as to be capable of sliding between a downstream stable closure position where the plug closes said passage and where the needle does not pass through the plug, and an upstream position where said needle does pass through the plug and towards which the plug can be pushed by a member inserted in said passage from outside said connector, and means situated in the chamber resiliently urging the plug towards its stable closure position, the material of the plug being such that the plug retrieves its closure properties when the needle is not passing through it.

Such a unitary composite connector is particularly useful in medical applications, for example when injecting a liquid into the body of a patient, and various embodiments have been described, in particular in Documents EP 0 309 771 and U.S. Pat. No. 4,998,927.

Those publications demonstrate that it is difficult to obtain a unitary composite connector of acceptable manufacturing costs that provide reliable and effective coupling and that is free from any danger of contamination.

An object of the invention is to provide a novel unitary composite connector of the above-described type, suitable for providing a coupling that is reliable and effective, that is of acceptable manufacturing cost, particularly if the connector is to be discarded after use, and that does not present any risk of contaminating the liquid circuit, in particular in the region of its downstream coupling.

SUMMARY OF THE INVENTION

According to the invention this is achieved by said passage of the downstream coupling has an outlet opening that is completely filled by the material of the plug when the plug is in its stable closure position, thereby preventing any dead volume around the plug in the opening and thus preventing any risks of contamination relating to the presence of such a dead volume, and by said means resiliently urging the plug being a spring.

By using a spring to push back the plug where the prior art uses resilient deformation of a tubular portion of the plug itself is most important since it makes it possible to select the spring return force at will and to use a plug that is a force-fit in the downstream coupling such that the lateral compression of the plug in the coupling guarantees good sealing, the selected spring providing sufficient force to push the plug into the coupling in spite of the friction between the plug and the coupling due to the lateral compression of the plug.

BRIEF DESCRIPTION OF THE DRAWINGS

Embodiments of the invention are described by way of example with reference to the accompanying drawings, in which.

DETAILED DESCRIPTION

Figure 1:
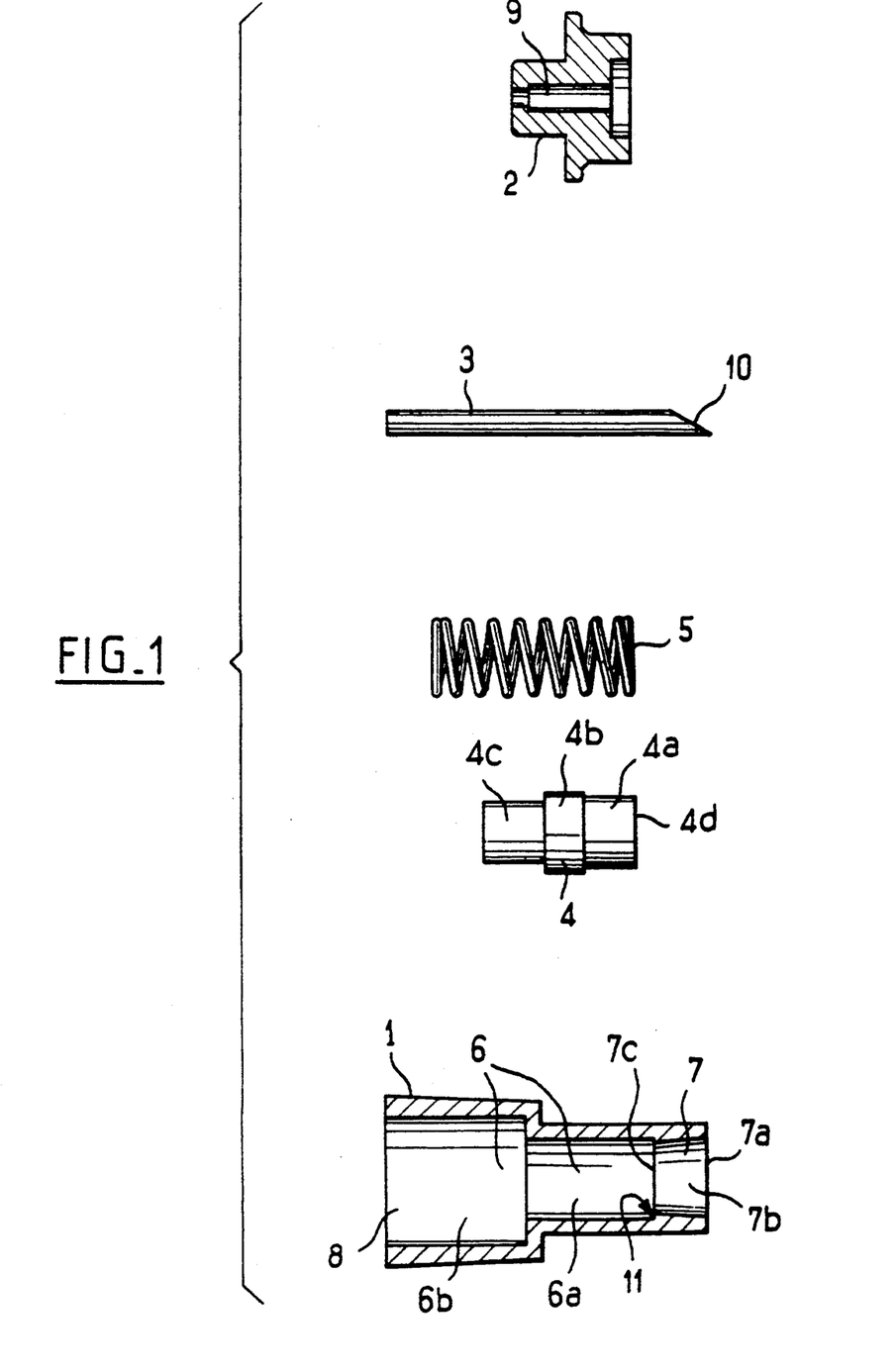
FIG. 1 is an exploded view of the component parts of a connector of the invention.

FIG. 1 shows the component parts of a first embodiment of a connector of the invention.

This connector comprises a rigid body constituted by a combination of five parts, namely:

a non-deformable case 1;
an upstream coupling 2;
a needle 3;
a closure plug 4; and
a helical spring 5.

These pieces are assembled together to constitute a unitary assembly (FIG. 2) taking account of the following features.

Figure 2:
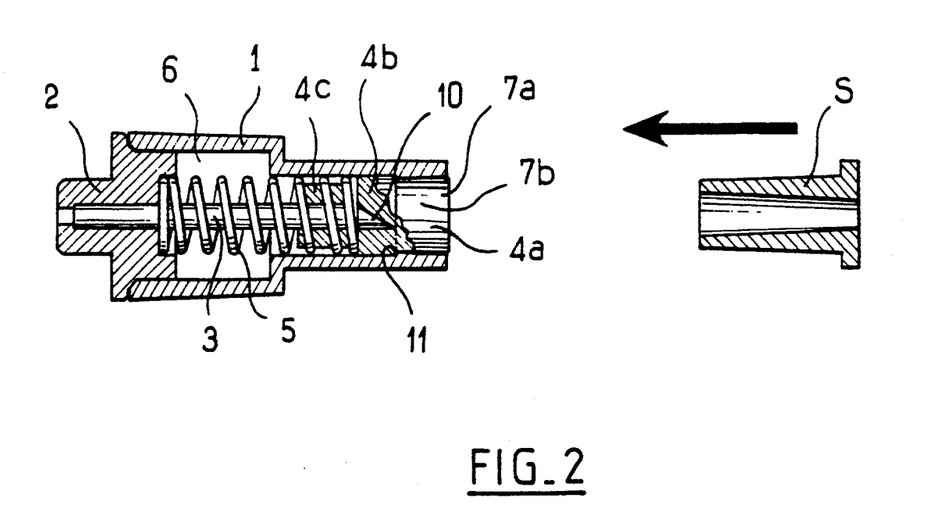
FIG. 2 is an axial section through the connector in its closed state.

The case 1 delimits a tubular chamber 6 between a downstream end 7 which is shaped to constitute a downstream coupling, and an upstream end 8 which is shaped to receive the upstream coupling 2. In this example, the chamber 6 has two zones 6a and 6b of different diameters.

The upstream coupling 2 has a central channel 9 which receives the needle 3 as a friction fit, such that when said coupling is assembled to the case, the needle penetrates axially into the chamber, thus extending towards the downstream coupling.

The downstream coupling 7 constitutes a frustoconical passage 7b with the outlet opening 7a of said passage being slightly greater in diameter than its inlet opening 7c. This type of passage is designed in a manner that is known per se for receiving an endpiece 12 having a complementary male conical shape.

Figure 3:
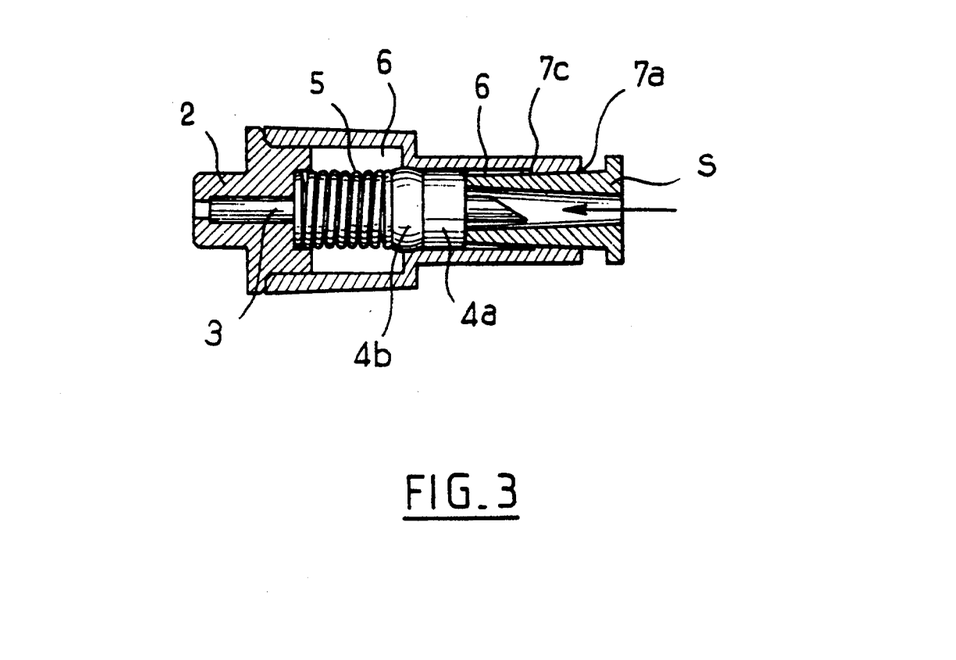
FIG. 3 is an axial section through the connector in its non-closed state.

The plug 4, the chamber 6, and the passage 7b are shaped so that the plug can slide in the chamber and in the passage with lateral sealing between a downstream position (FIG. 2) and an upstream position (FIG. 3).

The plug is a cylindrical block of elastomer having a downstream end 4a suitable for sliding in the passage 7b with lateral sealing, and an upstream end 4b of larger diameter suitable for sliding in the chamber 6 with lateral sealing. Its upstream end is preceded by a tail 4c used for engaging The spring 5 which comes into abutment against the upstream end.

In the downstream position (FIG. 2) the needle penetrates into the plug, but the chamfered opening 10 of the needle remains buried in the plug with the plug material closing said opening. The plug thus constitutes a closure member since the needle does not pass right through it, and in this way it prevents communication between the upstream coupling and the downstream coupling.

In the upstream position (FIG. 3) the plug has moved back towards the needle so that the passage 7b of the downstream coupling is completely disengaged, and so that the chamfered opening of the needle has passed right through the plug, with the opening then projecting beyond the plug: in this position, the upstream coupling and the downstream coupling are put into communication with each other by the needle.

The spring 5 is housed in the chamber 6 between the upstream coupling 2 against which it bears and the plug 4 which it urges towards its downstream position in which the plug is abutment against a shoulder constituted by an internal annular rim 11 of the chamber.

The spring is chosen so as to allow the plug to move through a stroke sufficient for it to move back against the action of the spring into an appropriate upstream position.

This backwards movement may be caused by inserting an endpiece S into the conical passage of the downstream coupling, e.g. the end of a syringe (FIGS. 2 and 3).

The passage of the downstream coupling and of the endpiece are conical, respectively female and male, thereby enabling the endpiece to be held in the coupling by friction.

If the endpiece is removed, then the plug returns automatically to its closure position under drive from the spring. The material from which the plug is made is such that the plug recuperates its closure properties when the needle no longer passes through the plug.

Such materials are known for this purpose and do not require describing in detail.

In its closure position, the plug completely fills the outlet opening 7a of the conical passage in the downstream coupling, and advantageously the plug has an end that bulges out a little from said outlet opening of the coupling (FIG. 2).

This avoids any risk of contaminants entering the passage of the coupling when the plug is in its closure position.

The upstream coupling 2 is of any suitable type and is generally constituted by a male coupling.

Figure 4A:
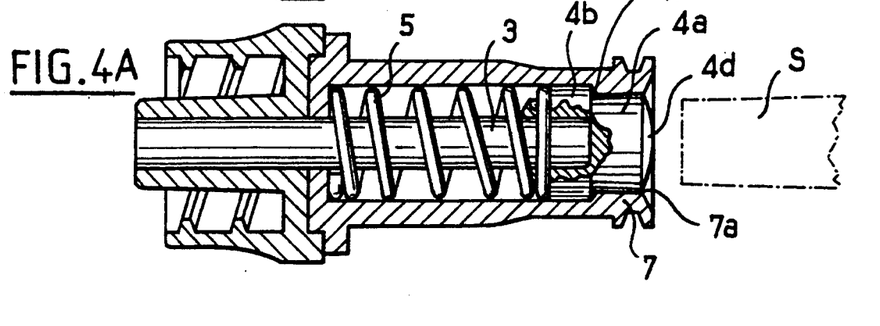
FIGS. 4A, 4B and 4C each is an axial section through a variant connector of the invention shown with the plug in three different positions.
Figure 4B:
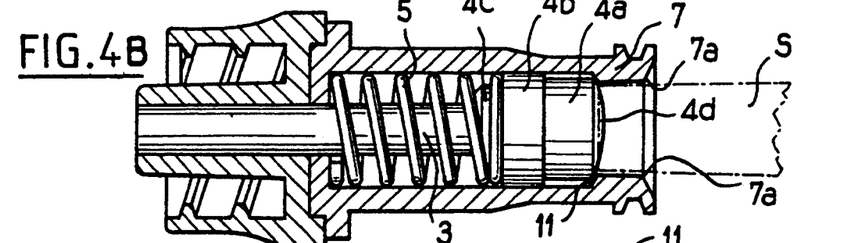
Figure 4C:
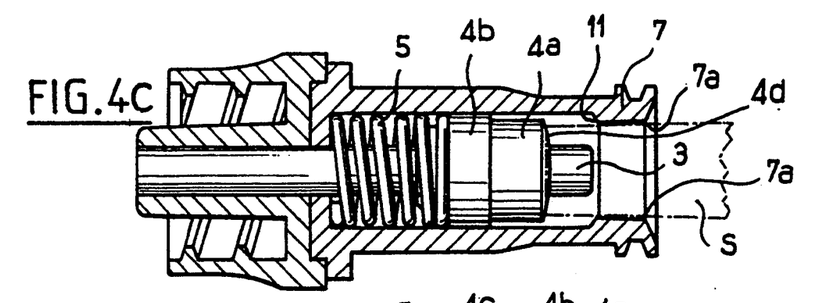

FIG. 4 shows an embodiment in which the needle 3 is merely a tube having a non-chamfered end that is embedded in the plug material, with the plug 4 having a downstream end 4a that is provided with a longitudinal pre-perforation 4e such that when it is at rest (i.e. when said end is not engaged on the needle) the pre-perforation 4e closes up (FIG. 4a), whereas when the plug is pushed towards the needle by an external element, e.g. the end of the syringe S, thrust from the needle causes the pre-perforation to open progressively so as to allow the needle to pass therethrough in a manner that is known per se (FIGS. 4B and 4C).

Figure 5:
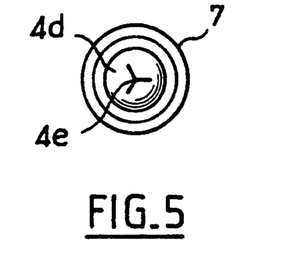
FIGS. 5 and 6 are end views of the plug in the downstream coupling in two different embodiments.
Figure 6:
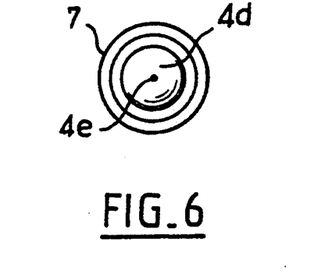

The pre-perforation may have any desired shape. For example, its right cross-section may be in the form of a cross (FIG. 5) or of a point (FIG. 6).

The plug shown in FIG. 4 has a cylindrical end 4a of diameter greater than the diameter of the outlet opening 7a of the passage 7b, which diameter is greater than the inlet diameter 7c of said passage. As a result, the spring 5 must be selected to provide sufficient force to push the plug into its closure position (FIG. 4A) where it is a force-fit. The end of the plug is thus compressed laterally in the downstream coupling 7, thereby ensuring lateral sealing of the coupling.

Figure 7:
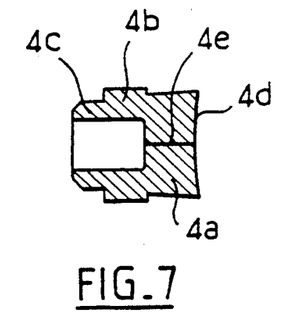
FIGS. 7 to 12 are axial sections through different embodiments of the plug.
Figure 8:
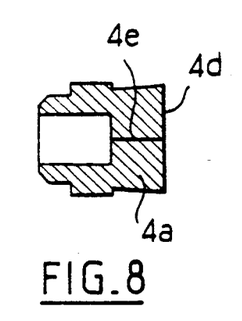
Figure 9:
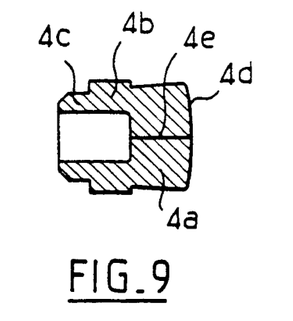

FIGS. 7 to 9 show embodiments in which the plug has a front face 4d that is concave (FIG. 7), flat (FIG. 8) or convex (FIG. 9), and an end 4a that flares going away from its front face 4d. The flare of this end substantially matches the internal frustoconical shape of the downstream coupling 7.

Figure 10:
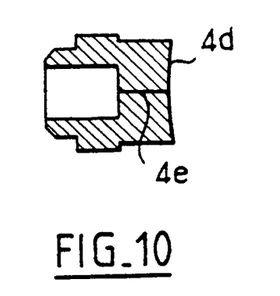
Figure 11:
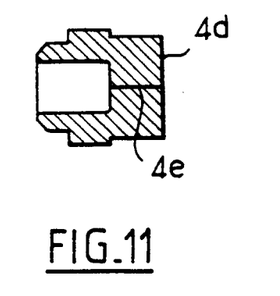
Figure 12:
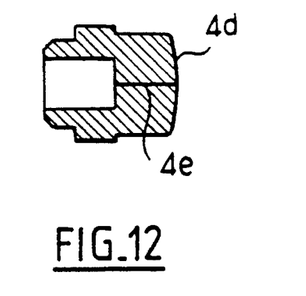

FIGS. 10 to 12 show embodiments in which the plug has a front face 4d that is concave (FIG. 10), flat (FIG. 11), or convex (FIG. 12), but in which the end of the plug 4a is cylindrical.

These various embodiments all have particular advantages either with respect to ease of manufacture, or with respect to ease of disinfection, or else with respect to the quality of the sealing that is obtained. Thus, a convex front face (FIGS. 2, 4, 9, 12) facilitate forcing the plug into the passage of the downstream coupling under thrust from the spring, a concave front face (FIGS. 7, 10) provide better decontamination opportunities, a flared shape (FIGS. 7 to 9) reduces friction forces as the plug reaches the end of its stroke under thrust from the spring, i.e. at the moment when the force from the spring is at its smallest.

The invention is not limited to a particular choice of upstream and downstream couplings, said choice depending on the conditions in which the connector is to be used.

Figure 13:
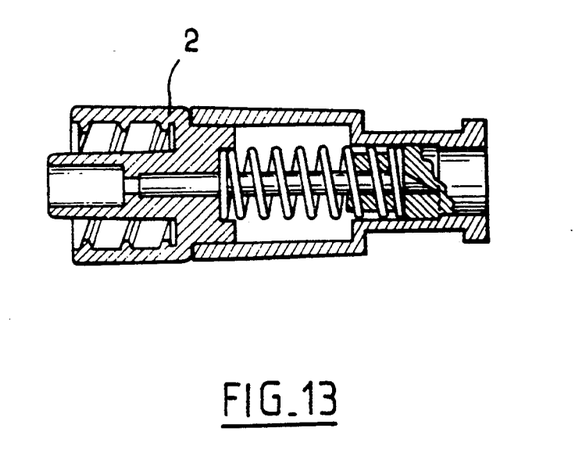
FIG. 13 is a sectional view showing an embodiment of a connector in accordance with the invention.

FIGS. 13 et seq. show non-limiting examples of connectors in accordance with the invention and provided with a variety of couplings. Some of the figures are in two parts showing respectively the connector when at rest (no communication) and in operation (communication).

Figure 14A:
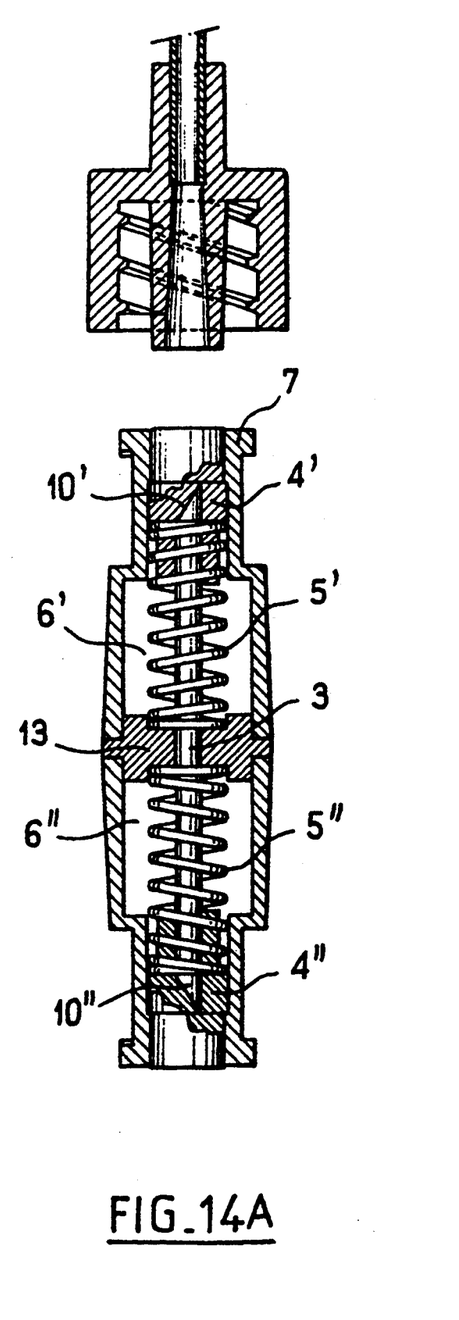
FIGS. 14A and 14B are sectional views showing an embodiment of a connector in accordance with the invention with FIG. 14A showing the connector in a rest or no communication condition and FIG. 14B showing the connector in an operative or communication condition.
Figure 14B:
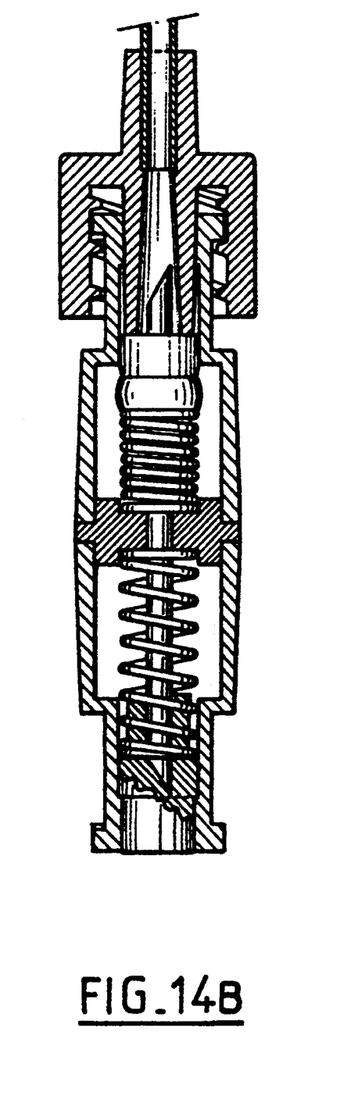
Figure 15A:
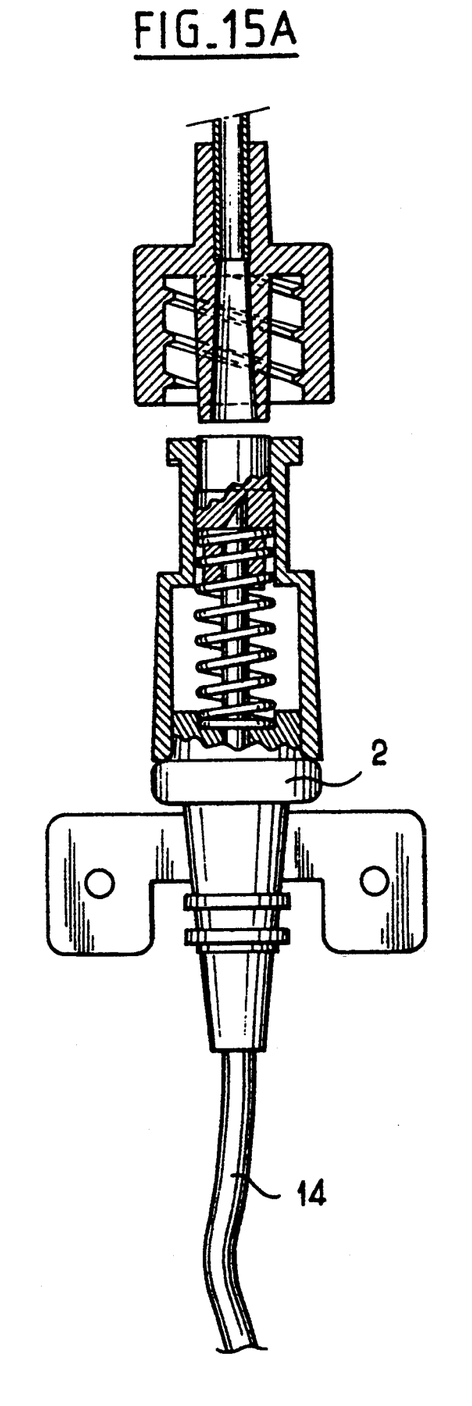
FIGS. 15A and 15B are sectional views showing an embodiment of a connector in accordance with the invention with FIG. 15A showing the connector in a rest or no communication condition and FIG. 15B showing the connector in an operative or communication condition.
Figure 15B:
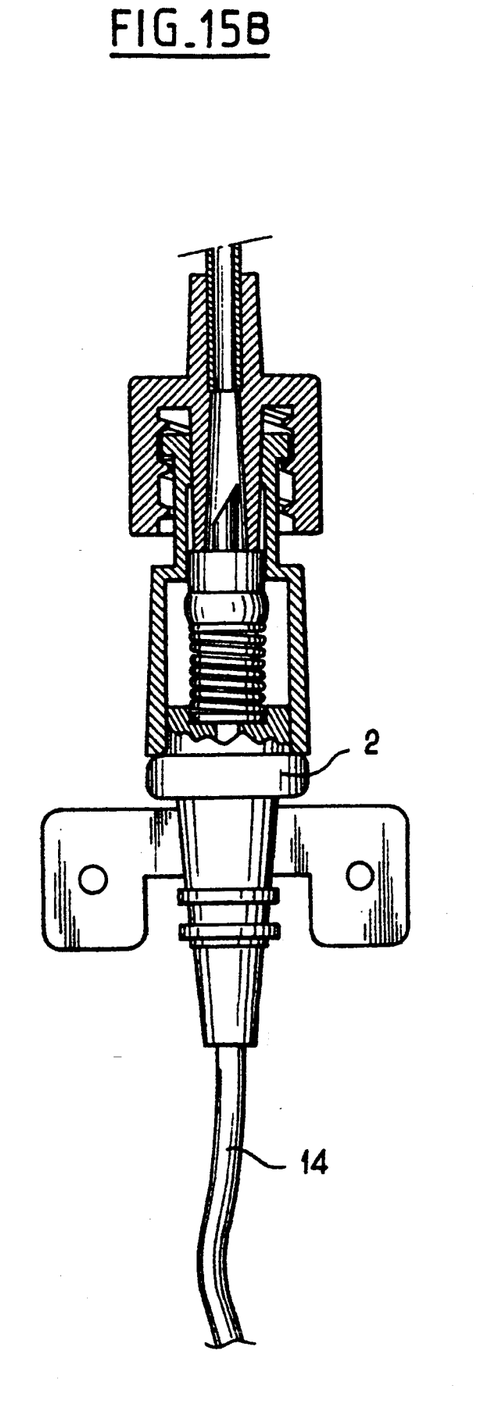
Figure 16A:
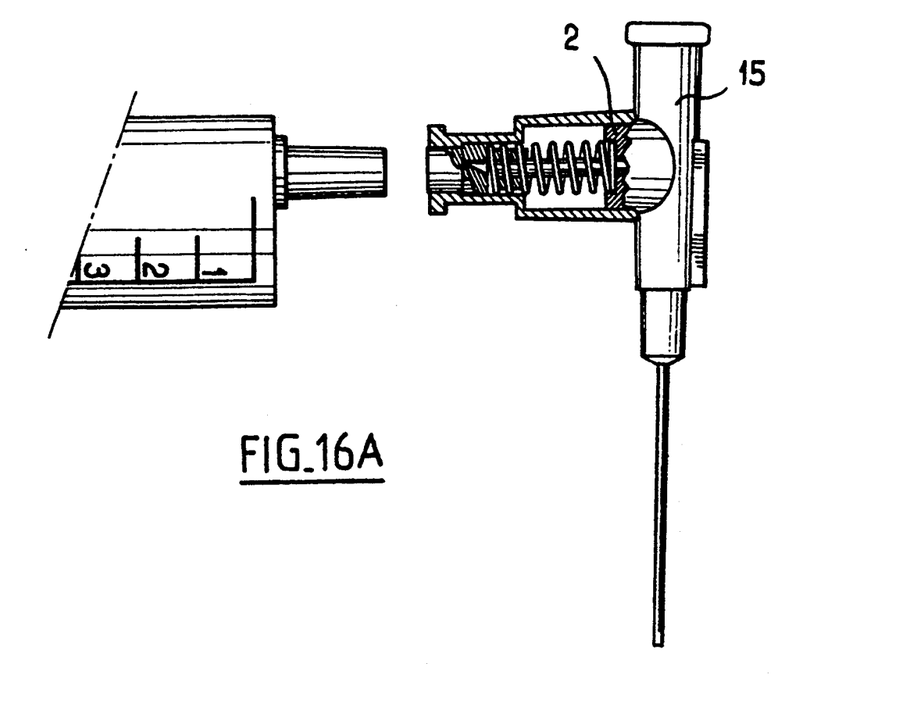
FIGS. 16A and 16B are sectional views showing an embodiment of a connector in accordance with the invention with FIG. 16A showing the connector in a rest or no communication condition and FIG. 16B showing the connector in an operative or communication condition.
Figure 16B:
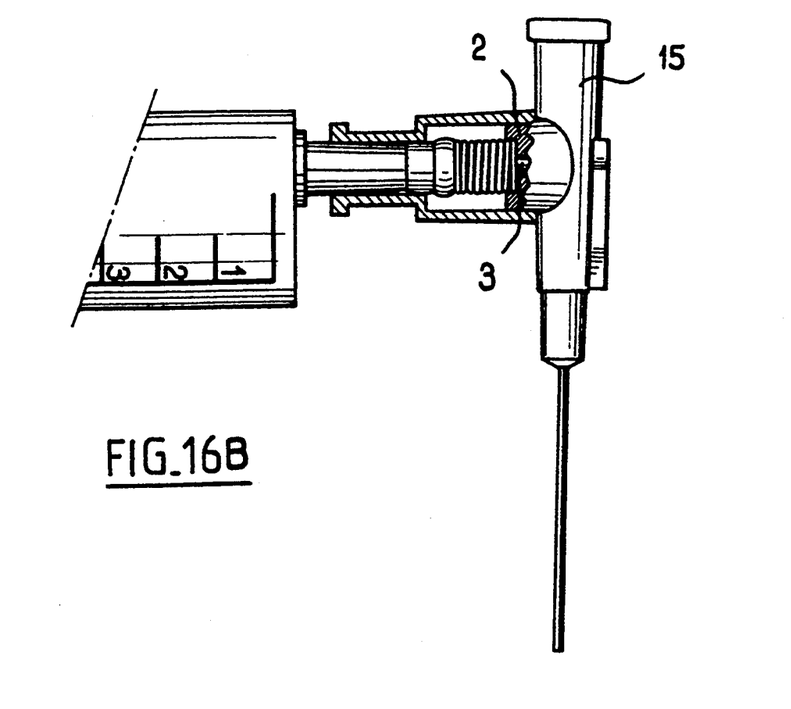
Figure 17:
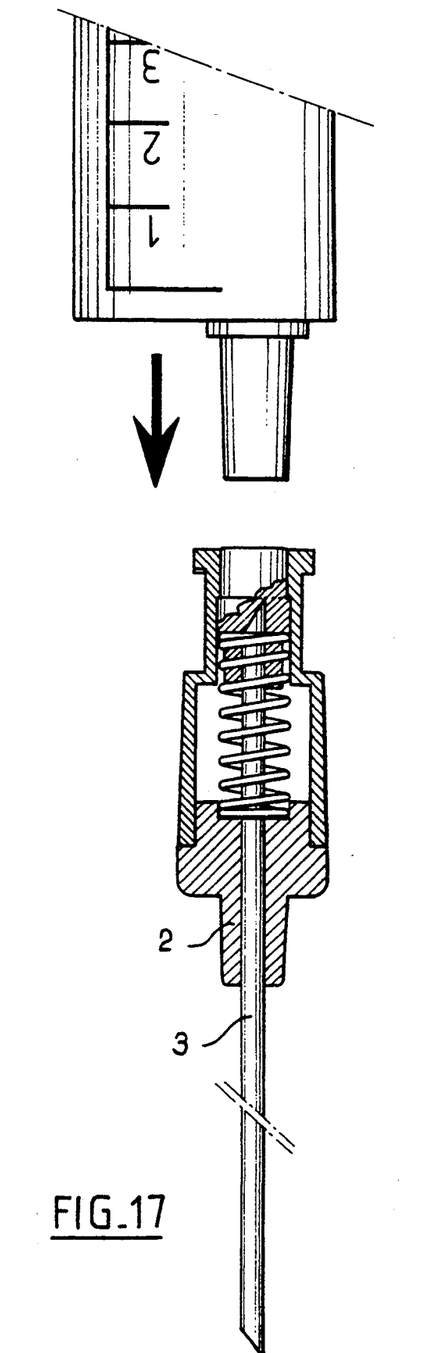
FIGS. 17-19 are sectional views showing embodiments of connectors in accordance with the invention.
Figure 18:
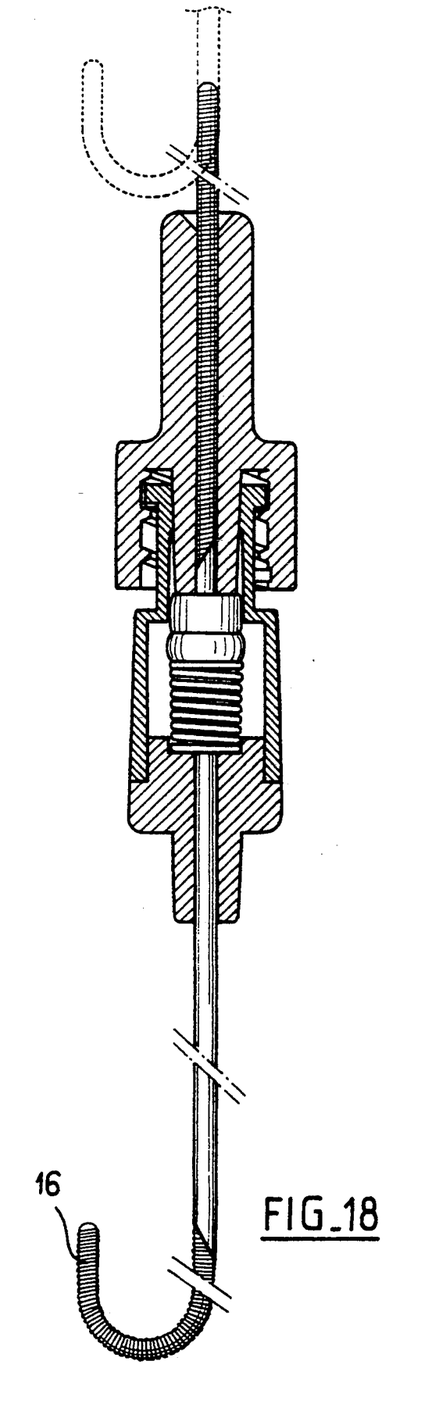
Figure 19:
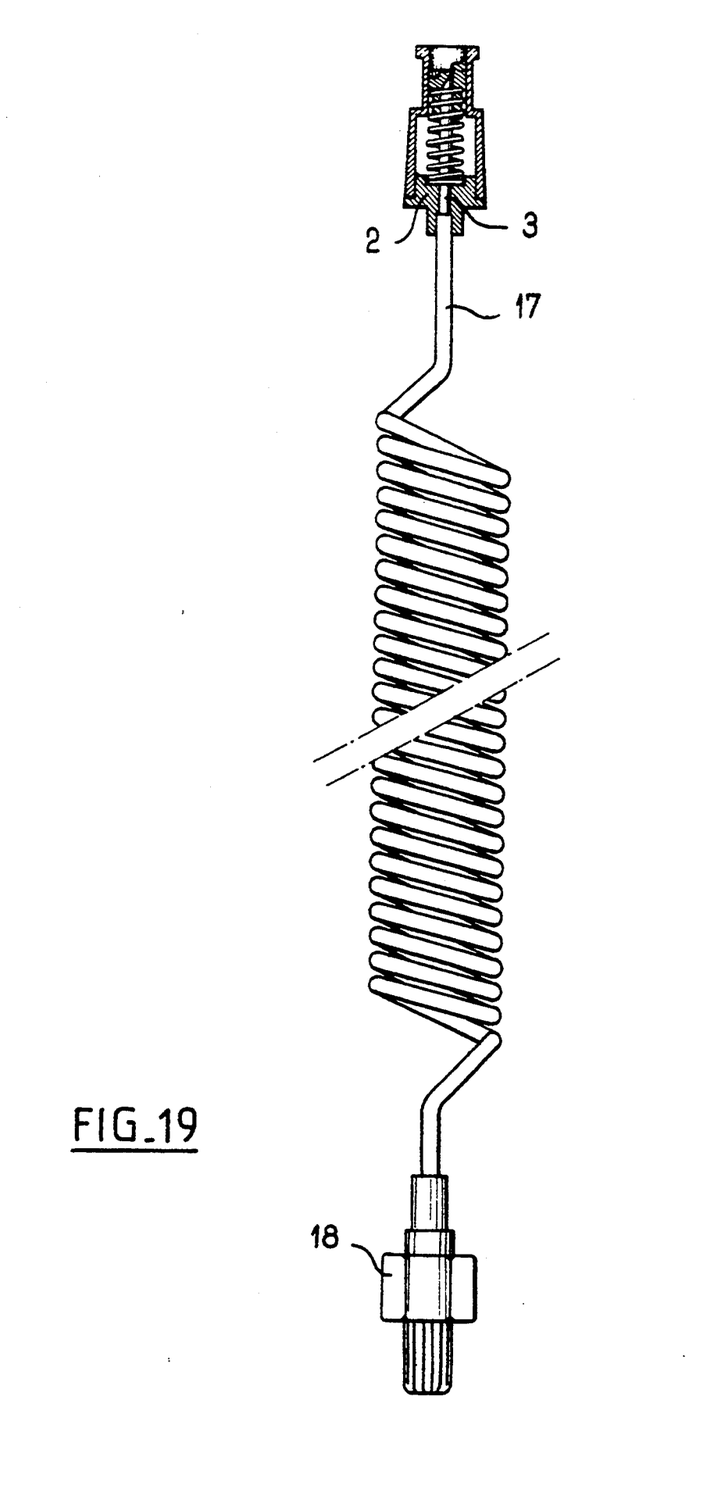
Figure 20A:
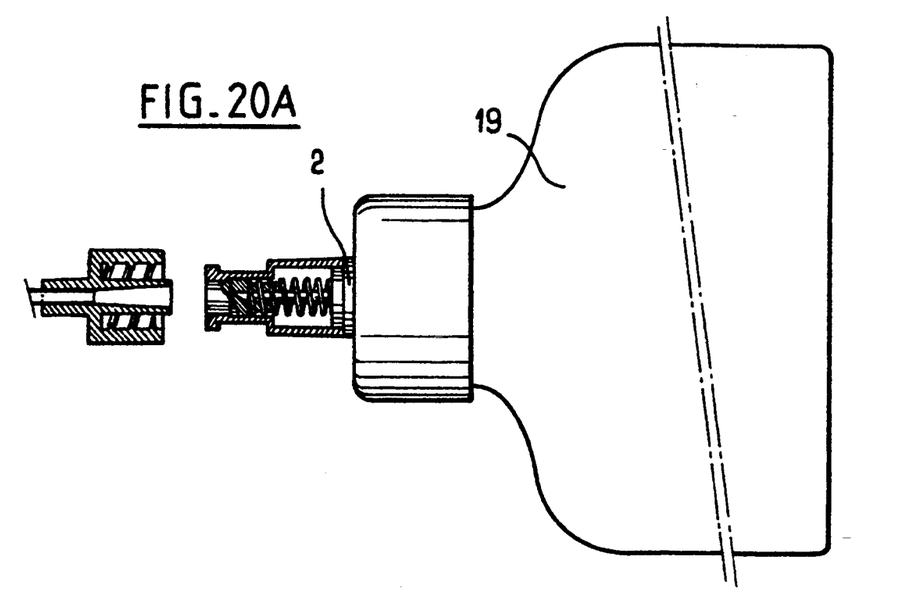
FIGS. 20A and 20B are sectional views showing an embodiment of a connector in accordance with the invention with FIG. 20A showing the connector in a rest or no communication condition and FIG. 20B showing the connector in an operative or communication condition.
Figure 20B:
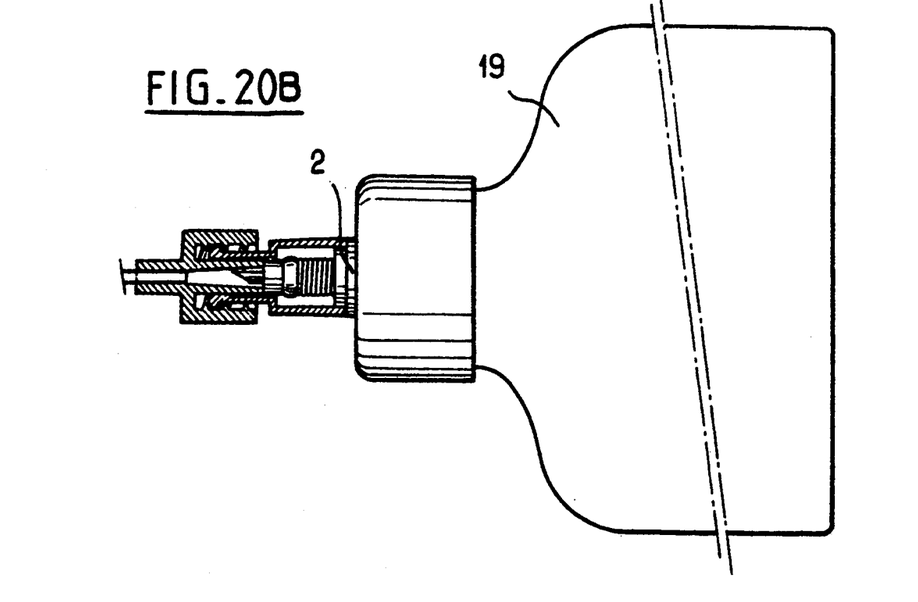

In these embodiments:

the upstream coupling 2 is of the male Luer lock type (FIG. 13);

the connector is symmetrical and double-ended (FIG. 14): the chamber is split into two compartments, respectively a downstream compartment 6' and an upstream compartment 6", the needle 3 is held in the chamber by a central support 13 through which it passes, and it has two opposite chamfered ends 10' and 10" pointing respectively towards the downstream coupling 7 and towards the upstream coupling 2, and two moving plugs 4' and 4" prevent communication respectively between the downstream compartment and the downstream coupling, and between the upstream compartment and the upstream coupling, each of the plugs being subjected to thrust from a corresponding spring 5', 5" which bears against the central support 13 and which urges the corresponding plug towards a position in which it is in abutment and the needle does not pass through it. In FIG. 14A, the connector is shown at rest with both plugs being in the closure position, while FIG. 14B shows the connector having one end in operation, and its other end at rest;

the upstream coupling 2 is secured to a tube 14 (FIGS. 15A and 15B);

the upstream coupling 2 is secured to an endpiece 15 which constitutes a duct extending transversely relative to the needle 3 (FIGS. 16A and 16B);

the needle 3 passes right through the upstream coupling 2 (FIG. 17);

the needle passes right through the upstream coupling and receives an internal metal guide 16 (FIG. 18);

the upstream coupling 2 is secured to a flexible tubular duct 17 having one end in communication with the needle and having its opposite end provided with a coupling 18 (FIG. 19); and the upstream coupling 2 constitutes a plug, e.g. a plug for a flask 19 (FIGS. 20A and 20B).

The terms "upstream" and "downstream" are used for designating the relative positions in the needle-to-plug direction. In operation, liquid will generally flow in the opposite direction such that if the liquid flow direction is taken as the reference, it becomes necessary to invert these terms: the "upstream" coupling should then be called the "downstream" coupling, the "outlet" opening of said coupling should then be considered as an "inlet" opening, etc.

The invention is not limited to the embodiments described above.

I claim:

1. A unitary composite connector for a liquid circuit, in particular for medical applications, the connector comprising:

means constituting a tubular chamber extending between an upstream coupling means extending from said chamber toward an upstream end of said connector and a downstream coupling means extending from said chamber toward a downstream outlet opening of said connector, said upstream coupling means including an upstream passage extending from said upstream end to said chamber and said downstream coupling means including a downstream passage extending from said chamber to said downstream outlet opening;

a hollow needle which is fixed in said upstream passage and which is disposed in said chamber for causing said upstream passage to be in fluid communication with said downstream passage; and a plug being made of material that permits said needle to be passed through it and that recaptures its closure properties whenever said needle is not passing through it, said plug being mounted in said downstream passage so as to be capable of sliding between a downstream stable closure position where the plug closes said downstream passage, where said needle does not pass through said plug, and where said plug completely fills said downstream outlet opening so as to prevent any dead volume at said downstream outlet opening to thereby prevent bacteria from entering said downstream passage, and an upstream position where said needle does pass through said plug and towards which said plug can be pushed by a member inserted in said downstream passage from outside said connector through said downstream outlet opening, and spring means situated in said chamber resiliently urging said plug towards its downstream stable closure position.

2. A connector according to claim 1, wherein said plug is a force-fit in said downstream coupling means.

3. A connector according to claim 1, wherein the plug slides with lateral sealing in said downstream coupling means and in said chamber.

4. A connector according to claim 1, wherein the stable, closure position is defined by an abutment against which the plug bears.

5. A connector according to claim 1, wherein said spring is received in the chamber between an abutment which carries the needle and the plug, said spring urging the plug towards its downstream position where the plug is in abutment against a shoulder constituted by an inside annular rim in said downstream coupling means.

6. A connector according to claim 1, wherein the plug has a concave end.

7. A connector according to claim 1, wherein the plug has a convex end.

8. A connector according to claim 1, wherein said downstream passage of said downstream coupling means includes a conical shaped portion extending from said downstream outlet opening.

9. A connector according to claim 8, wherein said plug has a conical shape complementary to that of said conical shaped portion of said downstream passage.

10. A connector according to claim 1, wherein said needle includes a chamfered end.

11. A connector according to claim 1, wherein the portion of the plug through which the needle is to pass includes a longitudinal perforation.

12. A connector according to claim 1, wherein when the plug is in its closure position, the end of the needle is embedded in the material of the plug.

13. A connector according to claim 1, wherein the upstream coupling means is a male coupling.

14. A connector according to claim 1, wherein the chamber is divided into two compartments, respectively a downstream compartment and an upstream compartment, the needle is held in the chamber by a support and has two opposite chamfered ends respectively pointing towards the downstream coupling means and towards the upstream coupling, means and wherein two moving plugs close off communication respectively between the downstream compartment and the downstream coupling, means and between the upstream compartment and the upstream coupling, means each of said plugs being subjected to the action of a spring which bears against the central support and which pushes the plug towards a position where it is in abutment and the needle does not pass therethrough.

15. A connector according to claim 1, wherein the upstream coupling means is secured to a tube.

16. A connector according to claim 1, wherein the upstream coupling means is secured to an endpiece which constitutes a duct disposed transversely relative to the needle.

17. A connector according to claim 1, wherein the needle passes right through the upstream coupling means.

18. A connector according to claim 1, wherein the needle passes right through the upstream coupling means and receives an internal metal guide.

19. A connector according to claim 1, wherein the upstream coupling means is secured to a tubular flexible duct having one communicating with the needle, and having its opposite end provided with a coupling.

20. A connector for a liquid comprising:
chamber means extending between an upstream coupling means and a downstream coupling means, said downstream coupling means having an outlet opening at one end of said connector;
a hollow needle means disposed in said chamber means for coupling said upstream coupling means to said downstream coupling means;
a plug means through which said needle means can be moved, said plug means being made of a material that has closure properties when said needle is not passing through it;
spring means disposed in said chamber means for urging said plug means to a downstream closure position where said plug means closes said outlet opening of said downstream coupling means by completely filling said outlet opening such that when said needle means does not pass through said plug means said outlet opening is completely filled by said material of said plug to thereby prevent any dead volume in said downstream outlet opening and to thereby prevent bacteria from entering said connector through said downstream coupling means; and
activating means insertable in said downstream coupling means through said outlet opening for moving said plug means towards an upstream open position where said needle means does pass through said plug means.

21. A connector according to claim 20 wherein said is a helical spring.

* * * * *

(12) EX PARTE REEXAMINATION CERTIFICATE (9009th)
United States Patent
Brinon (10) Number: US 5,380,306 C1
(45) Certificate Issued: May 15, 2012

(54) UNITARY COMPOSITE CONNECTOR FOR A LIQUID CIRCUIT, IN PARTICULAR FOR MEDICAL APPLICATIONS

(75) Inventor: Thierry Brinon, Ecouen (FR)

(73) Assignee: Vygon, Ecouen (FR)

Reexamination Request:
No. 90/010,323, Oct. 20, 2008

Reexamination Certificate for:
Patent No.: 5,380,306
Issued: Jan. 10, 1995
Appl. No.: 07/980,547
Filed: Nov. 23, 1992

(30) Foreign Application Priority Data

Nov. 25, 1991 (FR) .............................................. 91 14492

(51) Int. Cl.
*A61M 5/00* (2006.01)

(52) U.S. Cl. .......................... 604/244; 604/905; 128/764
(58) Field of Classification Search .......................... None
See application file for complete search history.

(56) References Cited

To view the complete listing of prior art documents cited during the proceeding for Reexamination Control Number 90/010,323, please refer to the USPTO's public Patent Application Information Retrieval (PAIR) system under the Display References tab.

*Primary Examiner* — Aaron J. Lewis (57) ABSTRACT

A hollow needle fixed in a chamber establishes a connection between an upstream coupling and a downstream coupling when it passes through a plug. The plug is made of a material such that it regains its closure properties when the needle is no longer passing through it, and it is pushed away from the needle by a spring to a closure position in which it fills the outlet opening of the downstream coupling. The connector is particularly suitable for use in medical applications.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-13 and 15-21 are cancelled.
Claim 14 was not reexamined.

\* \* \* \* \*